United States Patent [19]

Leising et al.

[11] Patent Number: 5,108,636

[45] Date of Patent: Apr. 28, 1992

[54] MAGNETIZABLE COMPOSITE PARTICLES BASED ON CROSSLINKED ORGANOPOLYSILOXANE, PROCESS FOR PREPARATION THEREOF AND THEIR APPLICATION IN BIOLOGY

[75] Inventors: Frederic Leising, Mornant; Ghislaine Torres, Lyons, both of France

[73] Assignee: Rhone-Poulenc Chimie, Courbevoie Cedex, France

[21] Appl. No.: 607,102

[22] Filed: Oct. 31, 1990

Related U.S. Application Data

[60] Division of Ser. No. 536,954, Jun. 12, 1990, Pat. No. 4,985,166, which is a continuation of Ser. No. 285,756, Dec. 16, 1988, abandoned.

[30] Foreign Application Priority Data

Dec. 18, 1987 [FR] France .................................. 87 17718

[51] Int. Cl.⁵ .......................... H01F 1/26; H01F 1/28; C12N 11/08; C12N 11/14
[52] U.S. Cl. .............................. 252/62.54; 252/62.53; 428/403; 428/405; 435/176; 435/180; 435/188
[58] Field of Search .......................... 252/62.53 62.54; 428/403, 405; 435/176, 180, 188; 427/213.3, 213.31, 213.32, 213.33, 213.34, 213.35, 213.36, 219

[56] References Cited

U.S. PATENT DOCUMENTS

| | | | |
|---|---|---|---|
| Re. 32,573 | 1/1988 | Furumura et al. | 252/62.56 |
| 4,271,234 | 6/1981 | Shonafinger et al. | 252/62.56 |
| 4,356,098 | 10/1982 | Chagnon | 252/62.53 |
| 4,695,392 | 9/1987 | Whitehead et al. | 252/62.54 |
| 4,695,393 | 9/1987 | Whitehead et al. | 252/62.54 |
| 4,874,667 | 10/1989 | Lee et al. | 427/213.34 |
| 4,876,039 | 10/1989 | Lo et al. | 427/213.33 |

FOREIGN PATENT DOCUMENTS 621366 8/1978 U.S.S.R. ......................... 427/213.31

*Primary Examiner*—Michael Lewis
*Assistant Examiner*—Stephen G. Kalinchak
*Attorney, Agent, or Firm*—Finnegan, Henderson, Farabow, Garrett and Dunner

[57] ABSTRACT

Magnetizable composite particles, optionally in aqueous dispersion, consisting of a matrix based on a crosslinked organopolysiloxane, optionally bearing nonvinyl reactive and/or ionic units and magnetizable components less than 300 angstroms in diameter encapsulated in the matrix. The magnetizable composite particles are prepared by homogenizing a solution of the organopolysiloxane, an organohydrogenopolysiloxane optionally bearing ionic and/or reactive units, and a magnetic fluid, in the presence of water and a surfactant, performing a hydrosilylation in an aqueous emulsion, removing the organic solvents and the organic carrier liquid, and at least partially removing the water. The magnetizable composite particles are useful in biological applications.

25 Claims, No Drawings

MAGNETIZABLE COMPOSITE PARTICLES BASED ON CROSSLINKED ORGANOPOLYSILOXANE, PROCESS FOR PREPARATION THEREOF AND THEIR APPLICATION IN BIOLOGY

This is a division of application Ser. No. 07/536,954, now U.S. Pat. No. 4,985,186, filed June 12, 1990, which was a continuation of Ser. No. 07/285,756, filed Dec. 16, 1988 (abandoned).

BACKGROUND OF THE INVENTION

The present invention relates to magnetizable composite particles based on crosslinked organopolysiloxane, to a process for preparation thereof and to their application in biology.

According to the invention, the magnetizable composite particles may be utilized alone or in aqueous dispersion and comprise a matrix based on a crosslinked organopolysiloxane derived from the hydrosilylation of:

at least one organopolysiloxane SiVi containing, per molecule, at least two vinyl groups each linked to a silicon atom, the SiVi having a viscosity of 20 to 30,000,000 mPas at 25° C. and optionally bearing non-vinyl reactive and/or ionic units linked to a silicon atom or to a carbon atom of a hydrocarbon group joined to the organopolysiloxane chain via a Si-C bond;

with at least one organohydrogenopolysiloxane SiH, containing, per molecule, at least three hydrogen atoms each linked to a silicon atom, having a viscosity of 5 to 1,500 mPas at 25° C., and preferably between 20 and 150 mPas at 25° C., and optionally bearing non-vinyl reactive and/or ionic units linked to a silicon atom or to a carbon atom of a hydrocarbon group joined to the organohydrogenopolysiloxane chain via a Si-C bond; and encapsulated in the matrix, magnetizable components having a diameter less than 300 angstroms, and preferably ranging from 80 to 120 angstroms, the components being coated with a non-water soluble dispersing agent.

The organopolysiloxanes SiVi may be represented by the following formula I $$R''R'SiO(SiRR'''O)_n(SiR'''R'O)_nSiRR'R'' \quad (I)$$

wherein:

the R radicals may be identical or different, and represent a $C_1$-$C_4$ alkyl, phenyl or 3,3,3-trifluoropropyl radical;

the R' radicals may be identical or different, and represent R or a vinyl radical, the number of vinyl radicals being at least 2 per macromolecule;

the R'' radicals may be identical or different and represent R or an OH radical;

the R''' radicals may be identical or different and represent R or a unit -r-X, where r is a divalent organic radical and X is a non-vinyl reactive and/or ionic group;

at least 60% of the radicals represented by R, R' and R'' are methyl radicals;

n or m can independently be zero, R' representing a vinyl radical if m is zero, and n and m have a value sufficient to provide a polymer having a viscosity of 20 mPas to 30,000,000 mPas at 25° C., and sufficient also to provide a total number of -r-X units contributed by the organopolysiloxane SiVi and the organohydrogenopolysiloxane SiH preferably ranging from 1:1 to 1000:1, and more preferably ranging from 5:1 to 500:1, per molecule obtained from the hydrosilylation of organopolysiloxane SiVi with organohydrogenopolysiloxane SiH.

Examples of the organopolysiloxane SiVi include: the polymers of formula II $$(CH_2=CH)R_2Si-O-(RR'''Si-O)_n-SiR_2(CH=CH_2) \quad (II)$$

wherein R and R''' have the definition given above, n having a value sufficient to achieve a polymer viscosity of 20 mPas to 30,000,000 mPas at 25° C.; and the polymers of formula III $$R'''R'RSi-O(RR''R'Si-O)_n-[(CH_2=CH)R'''Si-O-]_m-SiRR'R'' \quad (III)$$

wherein R, R', R'' and R''' have the meaning given above, n and m having a value sufficient to achieve a polymer viscosity of 20 mPas to 30,000,000 mPas at 25° C.

The organohydrogenopolysiloxane SiH can be linear, branched or cyclic.

Preferred organohydrogenopolysiloxanes SiH include those of formula IV:

$$YR_2SiO(RR'''SiO)_p(YRSiO)_qSiR_2Y \quad (IV)$$

in which formula the symbols R are identical or different and have the definition given above with at least 80% of methyl radicals, the symbol Y denotes R or a hydrogen atom, the number of hydrogen atoms being at least 3 per molecule of polymer, and the symbol R''' has the definition given above, p and q having values sufficient to provide a viscosity for the polymer SiH preferably ranging from 5 to 1,500 mPas at 25° C., and more preferably ranging from 20 to 150 mPas at 25° C., and sufficient also to provide a total number of -r-X units contributed by the organopolysiloxane SiVi and the organohydrogenopolysiloxane SiH preferably ranging from 1:1 to 1000:1, and more preferably ranging from 5:1 to 500:1, per molecule obtained from the hydrosilylation of organopolysiloxane SiVi with organohydrogenopolysiloxane SiH.

Divalent organic radicals represented by r within the scope of the invention include, but are not limited to, the following:

$C_1$-$C_{18}$ linear or branched alkylene radicals, optionally extended with 1 to 5 divalent ethylenamine groups, with 1 to 50 $C_1$-$C_3$ alkylene oxide groups or with an $$-O-CH_2-CH(OH)-CH_2-$$

group; and polyoxyalkylene radicals containing from 1 to 50 $C_1$-$C_3$ oxyalkylene units.

Examples of divalent radicals within the scope of the invention include, but are not limited to, the following:

$-CH_2-$; $-(CH_2)_2-$; $-(CH_2)_3-$; $-CH_2-CH(CH_3)-CH_2-$;

$-(CH_2)_{10}-$; $-(CH_2)_{12}-$; $-(CH_2)_3NH-CH_2-CH_2-$;

-continued

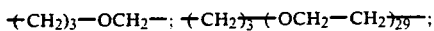

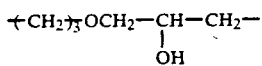

Reactive or ionic groups represented by X within the scope of the invention include, but are not limited to, the following: epoxy, hydroxy, carboxy, aldehyde, ester, aceto-ester, mercapto, mercapto ester, mercaptoalkoxy, amino, alkylamino, dialkylamino, trialkylamino, quaternary ammonium, amino alcohol, amido, hydrazide, hydrazino, $C_1$-$C_3$ haloalkyl, halobenzyl, cyano, cyanato,

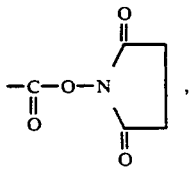

sulfate and sulfonyl.

Polymers SiVi and SiH not bearing non-vinyl reactive and/or ionic units are well-known. They are described, for example, in U.S. Pat. Nos. 3,220,972, 3,344,111 and 3,436,366, the disclosures of which are specifically incorporated by reference herein.

The polymers SiVi and SiH bearing non-vinyl reactive and/or ionic groups may be prepared according to well-known methods.

The polymers SiVi bearing non-vinyl reactive and/or ionic groups may be prepared by, for example:
  equilibration of a cyclotetrasiloxane and a vinylcyclotetrasiloxane in the presence of a functionalized disiloxane;
  equilibration of a functionalized cyclotetrasiloxane in the presence of a divinyldisiloxane; and
  equilibration of a functionalized polysiloxane oil in the presence of a divinylsiloxane and/or a cyclotetrasiloxane.

All starting materials set forth in the above exemplary methods of preparing the polymers SiVi are either commercially available or may themselves be prepared by one of ordinary skill in the art by routine means.

The polymers SiH bearing non-vinyl reactive and/or ionic groups may be prepared, for example, by:
  equilibration of a cyclotetrasiloxane and a polysiloxane oil containing internal SiH groups in the presence of a functionalized disiloxane which is not reactive with respect to SiH groups;
  equilibration of a functionalized cyclotetrasiloxane, which is not reactive with respect to SiH groups, in the presence of a dihydrogenodisiloxane; and
  equilibration of a functionalized polysiloxane, which is not reactive with respect to SiH groups, in the presence of a dihydrogenodisiloxane or a polysiloxane containing internal SiH groups.

All starting materials set forth in the above exemplary methods of preparing the polymers SiH are either commercially available or may themselves be prepared by one of ordinary skill in the art by routine means.

In a preferred embodiment of the invention, the matrix based on crosslinked polyorganosiloxane is derived from the hydrosilylation of at least one organopolysiloxane SiVi and at least one organohydrogenopolysiloxane SiH, wherein the ratio of the number of "SiH groups" (hydrogen atom linked to a silicon atom) to "SiVi groups" (vinyl group linked to a silicon atom) is preferably from 0.75:1 to 4:1, and more preferably from 0.75:1 to 1.5:1.

The materials capable of forming the magnetizable components encapsulated in the polyorganosiloxane matrix include, but are not limited to, the following: magnetite, hematite, chromium dioxide, ferrites such as ferrites of manganese, nickel, manganese-zinc, etc., and alloys of cobalt, nickel, gadolinium, samarium-cobalt, etc. The preferred materials are magnetite and hematite.

The quantity of magnetizable components encapsulated in the polyorganosiloxane matrix preferably corresponds to approximately 0.5 to 50% by weight relative to the weight of matrix, and more preferably ranges from 0.5 to 35% by weight.

Dispersing agents that can form a non-water-soluble coating around the magnetizable components include, but are not limited to, the following: fatty acids, amines, amides, etc., containing at least 12 carbon atoms, and preferably fatty acids containing approximately 18 carbon atoms such as oleic, linoleic and linolenic acids.

Silicone dispersing agents may also advantageously be utilized, such as those of formula V:

$$R_3SiO(R_2SiO)_x(R_2Si)_yZ \qquad (V)$$

wherein:
  R has the definition given above, and preferably represents a methyl radical;
  x is an integer ranging from 0 to 1,000;
  y is an integer equal to 0 or 1;
  Z represents a group that can be coordinated with the magnetizable components, such as a hydroxyl, SH, $NH_2$ radical, etc., or an alkyl radical substituted with a functional group such as, for example, the radicals—$(CH_2)_3NH_2$; —$(CH_2)_3SH$;
  —$(CH_2)_3$—NH—$C_2H_5$; —$(CH_2)_3NH$—$(CH_2)_2NH_2$;

—$(CH_2)_3$—NH—$C_2H_5$; —$(CH_2)_3NH$—$(CH_2)_2NH_2$;

—O—CO—$CH_2$—$COCH_3$;

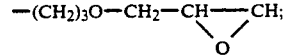

—$(CH_2)_3$—S—$CH_2$—COOH;

—$(CH_2)_3$—O—CO—$CH_2$—SH; —$CH_2$—COOH, etc.

—$(CH_2)_3$—S—$CH_2$—COOH;
—$(CH_2)_3$—O—CO—$CH_2$—SH;   —$CH_2$—COOH, etc.

The magnetizable particles of the invention may be uniform in diameter or may be within a range of particle diameters; their diameter preferably ranges from 0.05 to 3 microns, and more preferably ranges from 0.2 to 2 microns.

The magnetizable particles of the invention may be provided alone or as a dispersion in water. The quantity of magnetizable particles in the dispersed state in water preferably corresponds to approximately 10 to 70% by weight relative to the total weight of the dispersion, and more preferably ranges from 15 to 50% by weight.

The present invention also relates to a process for preparing the magnetizable composite particles.

The process comprises:
introducing, into an aqueous medium containing at least one surfactant, a mixture of:
- a solution of at least one organopolysiloxane SiVi as defined above, in an organic solvent having a boiling point below 100° C., or capable of forming with water an azeotrope having a boiling point below 100° C., and preferably below 95° C.;
- a solution of at least one organohydrogenopolysiloxane SiH as defined above, in an organic solvent having a boiling point below 100° C., or capable of forming with water an azeotrope having a boiling point below 100° C., and preferably below 95° C.; and
- a magnetic fluid consisting of magnetizable particles less than 300 angstroms, preferably ranging from 80 to 120 angstroms in diameter, suspended in an organic carrier liquid which is a solvent for the polymers SiVi and SiH and has a boiling point below 100° C. or is capable of forming with water an azeotrope having a boiling point below 100° C., and preferably below 95° C.;

homogenizing the medium obtained;
performing a hydrosilylation of the polymers SiH and SiVi in an aqueous emulsion;
removing the organic solvents and the organic carrier liquid; and
optionally, at least partially removing the water.

Solvents for the polymers SiVi and SiH which can be employed include, but are not limited to, the following: cyclohexane, methylene chloride, benzene, hexane, octane, toluene and carbon tetrachloride.

The solvent is employed to obtain a viscosity of the solutions of less than 1,000 mPas at 25° C., and preferably less than 500 mPas. It will be understood by those skilled in the art that a solvent may not be necessary when the molecular weight of one or more of the polymers is sufficiently low.

Magnetic fluids are commonly referred to in the art as "ferrofluids". They are extremely stable colloidal suspensions of ferro- or ferrimagnetic components less than one micron in diameter, in a carrier liquid, and remain fluid in the presence of external magnetic fields.

The type of material that is capable of forming ferro- or ferrimagnetic components has already been mentioned above. The preferred materials are magnetite and hematite.

According to the invention, the carrier liquid can be any of those organic liquids which were mentioned as solvents for the polymers SiVi and SiH having a boiling point below 100° C. or capable of forming with water an azeotrope having a boiling point below 100° C. While being of the same type, the carrier liquid used for the magnetic fluid may be similar to or different from the solvent employed for the polymers.

The magnetic fluid may be prepared in a known manner by the peptization in a dispersing agent of particles of magnetizable components obtained by grinding or by precipitation by the sol-gel method, followed by dispersion of the peptized particles in an organic carrier liquid. The dispersing agents which are useful in the preparation of the magnetic fluid can be fatty acids, amines, amides, etc., containing at least 12 carbon atoms, and preferably fatty acids containing approximately 18 carbon atoms such as oleic, linoleic and linolenic acids, as well as the silicone dispersants of formula V mentioned above.

The concentration of the magnetizable components in the magnetic fluid preferably ranges from 20 to 60% by weight and more preferably ranges from 30 to 60% by weight.

The quantity of magnetic fluid employed for carrying out the process of the invention is preferably such that the weight of magnetizable components in the magnetic fluid corresponds to approximately 0.5 to 50% of the weight of the polymers SiVi and SiH, and more preferably ranges from 0.5 to 35%.

The aqueous medium into which the mixture of solutions of polymers SiVi and SiH and magnetic fluid is introduced preferably has a concentration by weight of surfactant ranging from 0.5 to 15%, and more preferably ranges from 1 to 10%.

The surfactant present in the aqueous medium into which the mixture of polymer solution and magnetic fluid is introduced can be any emulsifier of the nonionic, anionic or cationic type that is water-soluble or capable of forming micelles in water.

Nonionic surfactants that can be used in the invention include polyethoxylated fatty alcohols, polyethoxylated alkylphenols, polyethoxylated fatty acids, condensates of ethylene oxide and propylene oxide, polyethoxylated fatty amides, polyethoxylated fatty amines, fatty acid esters, ethanolamides and polyvinyl alcohol.

Anionic surfactants that can be used in the invention include alkyl sulfates, alkylsulfonates, alkylarylsulfonates, sulfosuccinates and sodium sulfosuccinates.

Cationic surfactants that can be used in the invention include halides of fatty amines; halides, sulfates, methyl sulfates and acetates of ethoxylated fatty amines; and $C_{10}$–$C_{18}$ quaternary ammonium halides.

The quantity of aqueous medium which can be employed is preferably such that the quantity of surfactant ranges from approximately 0.5 to 60% by weight, and more preferably ranges from 1 to 50% by weight, relative to the weight of polymers SiVi and SiH.

The operation of introducing the mixture of solutions of polymers SiVi and SiH and magnetic fluid into the aqueous medium is preferably carried out gradually with stirring at room temperature (generally 15° to 40° C.).

The homogenization operation is preferably carried out in one or more stages at a temperature ranging from 20° to 60° C., using a vigorous agitation system such as a colloid mill, high pressure pump, vibratory agitator, ultrasonic apparatus, etc., until a dispersion of droplets of the organic phase containing the magnetizable components is obtained. The droplets preferably range from approximately 0.065 to 3.2 microns, and more preferably range from 0.35 to 2.2 microns, in diameter. The droplets are comprised of polymers SiVi and SiH, swollen with solvent(s) and containing the magnetizable components.

The operation of crosslinking the polymers SiVi and SiH is preferably carried out using an effective quantity of a hydrosilylation catalyst.

Exemplary catalyst compounds that can be used in crosslinking polymers SiVi and SiH include: platinum group metal compounds, preferably salts and complexes of these compounds and more preferably the platinum-olefin complexes as described in U.S. Pat. Nos. 3,159,601 and 3,159,662; the reaction products of platinum derivatives with alcohols, aldehydes and ethers described in U.S. Pat. No. 3,220,972; the platinumvinylsiloxane catalysts described in French Patent No. 1,313,846 and its addition 88,676 and French Patent No. 1,480,409; the complexes described in U.S. Pat. Nos 3,715,334, 3,775,452 and 3,814,730; and also a rhodium catalyst as described in U.S. Pat. Nos. 3,296,291 and 3,928,629. All patent documents mentioned in this paragraph are specifically incorporated by reference herein.

The preferred metals of the platinum group are platinum and rhodium. Ruthenium, although much less active, is much cheaper, and also can be used.

The quantity of catalyst employed preferably ranges from 5 to 100 ppm, and more preferably ranges from 10 to 60 ppm, calculated as the weight of metal relative to the total weight of the polymers SiVi and SiH.

The catalyst is preferably introduced into the crosslinking medium in the form of an aqueous emulsion.

To prepare this aqueous emulsion, the catalyst is preferably introduced into a colloid mill with an emulsifier of the same type as that employed for preparing the surfactant solution described above, and water.

The catalyst emulsion is preferably introduced into the crosslinking medium after homogenization of the mixture of polymers SiVi and SiH/magnetic fluid/water, and after removal of the organic solvents and organic carrier liquid.

The medium is then heated to a temperature preferably ranging from 20° to 70° C., and more preferably ranging from 20° to 40° C.

This operation can range from 15 mins. to 4 hrs., and preferably ranges from 15 to 30 mins.

An aqueous dispersion is thereby obtained, containing preferably 10 to 60%, and more preferably from 15 to 50%, of its weight of composite particles which preferably range in diameter from 0.05 to 3 microns, and more preferably from 0.2 to 2 microns, and which are comprised of a matrix based on the crosslinked polyorganosiloxane (the degree of crosslinking preferably ranging from 40 to 100% and more preferably from 90 to 100%) and, encapsulated in the matrix, magnetizable components preferably less than 300 angstroms in diameter and more preferably ranging from 80 to 120 angstroms.

The weight of magnetizable particles in aqueous dispersion may be adjusted at will, either by the partial removal of the water after magnetization, or by the complete removal of the water after magnetization followed by addition of deionized water until a dry extract content preferably ranging from 10 to 70% by weight, and more preferably ranging from 15 to 50% by weight, is obtained.

The solvent or solvents for the polymers and the carrier liquid are preferably then removed by distillation under vacuum.

According to another embodiment of the invention, the solvent or solvents for the polymers and the carrier liquid are removed by distillation under vacuum immediately before the crosslinking operation. In this embodiment, the crosslinking operation is carried out during more than 2 hours and preferably takes approximately 4 hours.

If desired, the particles can be separated from the medium by simple magnetization.

The magnetizable particles of the invention possess features which make them useful, in particular, in biological applications.

The magnetizable particles of the invention possess the following advantages:

they may be sterilized by heating for 2 hours at 122° C., and they remain active after sterilization;

the magnetizable components which the particles contain can be coated with a silicone matrix, thereby avoiding any interaction between the magnetizable components and the reaction medium in which the particles are used;

they are biotolerant and non-toxic, and therefore do not interfere with biological processes in vitro and can be used in vivo; and they are magnetizable, which enables them to be separated by simple magnetization from the reaction medium in which they have been used, and as a result, washing operations also can be carried out more quickly.

The magnetizable particles may be used, for example, as active supports:

for antibodies or antigens for diagnostic testing and for affinity separations of biological compounds; the binding of biological molecules can, if necessary, be carried out by well-known coupling methods, involving coupling agents (glutaraldehyde, water-soluble carbodimide), or which alternatively consist of activating the possible functional groups of polyorganosiloxane (for example, by diazotization, by the action of cyanogen bromide or hydrazine, etc.) and reacting the molecule to be bound;

for enzyme systems for biological reactions;

for the attachment of cell cultures;

for medicinal products or for tracer substances, for guiding these products or substances in vitro or in vivo to the chosen point of treatment;

for chemical molecules, permitting growth of these molecules by a rapid concatenation of particular reactions, as in peptide synthesis;

for chemical groups which are reaction catalysts; and for chemical groups for the separation or extraction of metals or optical isomers.

The examples which follow are intended to be used as a guide, and should not be considered to limit the scope and spirit of the invention.

The ferrofluids employed for carrying out Examples 1-16 were prepared according to the following general procedures:

11 kg of $FeCl_3$19 $6H_2O$ and then 7.5 kg of $FeSO_4 \cdot 7H_2O$ were dissolved successively in 31 kg of water. The solution obtained was introduced into a reactor containing 20 kg of a 20% strength aqueous solution of ammonia. The reactor was brought to 60° C. and maintained at this temperature for 15 minutes; 2.4 kg of oleic acid were added and the medium was maintained with stirring at 60° C. for 15 minutes; the medium was cooled to 25° C. and then neutralized with 38% strength hydrochloric acid until a pH of 5.5 was obtained.

After vacuum filtration, the product was washed with water and then with acetone and dried. The product was taken up with an organic solvent (carrier liquid) and the residual water was then removed by azeotropic distillation.

The quantity of carrier liquid was such that the concentration of magnetite formed was 50% by weight.

The diameter of the magnetite components, measured by electron microscopy, was of the order of 100 angstroms.

EXAMPLE 1

13 g of a ferrofluid in which the carrier liquid was cyclohexane (corresponding to 6.5 g of magnetite) were introduced into a solution consisting of:
- 400 g of cyclohexane;
- 31 g of oil 50620 containing 3% by weight of vinyl groups, this oil being marketed by RHONE-POULENC, and consisting of a polydimethylsiloxane oil containing SiVi groups along, and at the ends of, the macromolecular chain; and
- 4 g of oil 628 V 30 H 10, marketed by RHONE-POULENC (this is a polydimethylsiloxane oil bearing SiH groups in a quantity corresponding to 1% by weight of hydrogen relative to the oil) which corresponds to a ratio of the concentration of reactive groups [SiH]/[SiVi] approximating 1:1.

The characteristics of the two oils are as follows:
SiVi oil—average degree of polymerization=300 viscosity=300–500 mPas at 25° C.
SiH oil—average degree of polymerization=100 viscosity=50 mPas at 25° C.

The mixture obtained was then homogenized in the presence of 800 g of water and 18.2 g of CEMULSOL ON 10–20 emulsifier containing 86.5% of active substance, marketed by SOCIETE FRANCAISE D'ORGANO SYNTHESE (which corresponds to 45% by weight relative to the silicone oils), in an ultrasonic trough (SONIFIER B-30 apparatus marketed by BRANSON SONIC POWER CO) for 10 minutes.

The emulsion thereby obtained possessed an average particle diameter (measurement performed in a COULTER NANOSIZER PSM series 17, marketed by Coulter Electronics Ltd) of 0.9–1 micron.

An emulsion of catalyst 70 889 (marketed by RHONE-POULENC, containing 5% by weight of complexed platinum) was then introduced in a quantity corresponding to 1/1,000 by weight of emulsion relative to the mixture of silicone oils. The mixture was maintained at 40° C. for 4 hours.

The cyclohexane was then removed at 40° C. under reduced pressure (175 mbar). The final traces of cyclohexane were removed by azeotropic distillation with acetic acid.

Gas chromatographic analysis of the residual cyclohexane revealed levels of less than 15 ppm.

A dispersion of particles having an average diameter of 0.7–0.8 micron, and containing 18.5% by weight of magnetizable components of the order of 100 angstroms in diameter was obtained.

The assessment of the degree of crosslinking of the particles, carried out by solvent extraction, revealed levels of the order of 95%.

The encapsulation of the magnetizable components was observed in the following manner:

100 mg of the dispersion of particles were introduced into 100 ml of acetone; the precipitate obtained, separated off and dried, was treated with 10 cm$^3$ of 1 N hydrochloric acid. After 24 hours, it was observed that there was no coloration either o the aqueous phase or of the surface of the particles.

The particles may be separated from the dispersion using a simple laboratory magnet. Similarly, the dispersion of particle may be washed by separation by magnetization of particles and replacement of the liquid phase by an aqueous solution of CEMULSOL ON 10–20 containing 1% of active substance.

EXAMPLE 2

The operation described in Example 1 was repeated, starting with:
- 13 g of the ferrofluid, which corresponds to 6.5 g of magnetizable pigment; and
- a solution of 400 g of cyclohexane, 31 g of oil 50620, and 5 g of epoxidized polydimethysiloxane oil bearing SiH groups, of formula $$(CH_3)_3SI[OSi(CH_3\text{ }_2]_{5.4}(OSiHCH_3)_{5.7}(O-SiCH_3)_{6.25}OSi(CH_3)_3$$
$$|$$
$$(CH_2)_3$$
$$|$$
$$O-CH_2-CH-CH_2$$
$$\diagdown\diagup$$
$$O$$

having the following characteristics:
Mn=2,000;
Concentration of the epoxide groups=2.29 milliequivalents/g of oil; and
Concentration of SiH groups=2.10 milliequivalents/g of oil The homogenization was carried out in the presence of 800 g of water and 15.75 g of sodium lauryl sulfate; the average particle diameter of the emulsion was 0.9 micron.

After crosslinking, a dispersion of particles whose average diameter was 0.85 micron, and containing 18.5% by weight of magnetizable components of the order of 100 angstroms in diameter, was obtained.

The degree of crosslinking was 97%.

Magnetization to saturation (measurement performed using a hysteresis meter at $2786\times10^2$ A/m)=6.8 e.m.u./g.

EXAMPLES 3 to 9

The operation described in Example 2 was repeated, carrying out the homogenization operation according to the conditions stated in Table I.

The characteristics of the dispersions of particles obtained after crosslinking under the conditions described in Example 2 are shown in Tables I and II.

EXAMPLE 10

The operation described in Example 2 was repeated replacing the oil 50620 by 31 g of oil 621 V 20, marketed by RHONE-POULENC; this is an α,ω-divinyl-polydimethylsiloxane oil whose characteristics are as follows:
Mn=1,800, and concentration of SiVi groups=1.07 milliequivalent/g of oil; and
then performing the crosslinking operation at 20° C. for 1 hour.

The characteristics of the dispersion of particles obtained are shown in Table II.

EXAMPLE 11

The operation described in Example 2 was carried out, employing 22.5 g of the ferrofluid, which corresponds to 11.25 g of magnetizable pigment.

The homogenization was carried out in the presence of 800 g of water and 18.2 g of CEMULSOL ON 10–20 containing 86.5% of active substance; the average particle diameter of the emulsion was 0.85 micron.

After crosslinking under the conditions described in Example 1 or 2, a dispersion of particles whose average diameter was 0.75 micron, and containing 32.1% by weight of magnetizable components of the order of 100 angstroms in size, was obtained.

The degree of crosslinking was 97%.

Magnetization to saturation = 24 e.m.u./g.

EXAMPLE 12

The operation described in Example 2 was carried out employing 43.4 g of the ferrofluid, which corresponds to 21.7 g of magnetizable pigment.

The homogenization was carried out in the presence of 800 g of water and 18.2 g of CEMULSOL ON 10-20 containing 86.5% of active substance; and the average particle diameter of the emulsion was 1.2 micron.

After crosslinking under the conditions described in Example 1 or 2, a dispersion of particles whose average diameter was 0.75 micron, and containing 62% by weight of magnetizable components, was obtained.

The degree of crosslinking was 92%.

Magnetization to saturation = 27 e.m.u./g.

EXAMPLE 13

The operation described in Example 1 was repeated, starting with:

13 g of the ferrofluid, which corresponds to 6.5 g of magnetizable pigment; and a solution of 400 g of cyclohexane, 31 g of oil 50620, and 4 g of a carboxymethylated polydimethylsiloxane oil bearing SiH groups, of formula

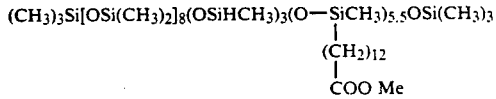

having the following characteristics:

Mn = 2,400;

Concentration of SiH groups = 1.25 milliequivalents/g of oil;

Concentration of carboxymethyl groups = 2.45 milliequivalents/g of oil.

The homogenization was carried out in the presence of 800 g of water and 18.2 g of CEMULSOL ON 10-20 containing 86.5% of active substance; the average particle diameter of the emulsion was 0.9 micron.

After crosslinking, the dispersion of particles whose average diameter was 0.7 micron, and containing 18.5% by weight of magnetizable components, was obtained.

The degree of crosslinking was 98%.

Magnetization to saturation = 6.7 e.m.u./g.

EXAMPLE 14

The operation described in Example 1 was repeated, starting with:

13 g of the ferrofluid, which corresponds to 6.5 g of magnetizable pigment; and a solution of 400 g of cyclohexane, 31 g of oil 50620, and 4 g of a carboxymethylated polydimethylsiloxane oil bearing SiH groups, of formula

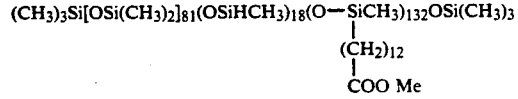

having the following characteristics:

Mn = 15,000;

Concentration of SiH groups = 1.25 milliequivalents/g of oil; and

Concentration of carboxymethyl groups = 8.8 milliequivalents/g of oil.

The homogenization was carried out in the presence of 800 g of water and 15.75 g of lauryl trimethylammonium chloride.

The average particle diameter of the emulsion was 1 micron.

After crosslinking, a dispersion of particles whose average particle diameter was 0.8 micron, and containing 18.5% by weigh of magnetizable components of the order of 100 angstroms in diameter was obtained.

The degree of crosslinking was of the order of 32%.

EXAMPLE 15

The operation described in Example 1 was repeated, starting with:

13 g of the ferrofluid, which corresponds to 6.5 g of magnetizable pigment; and a solution of 400 g of cyclohexane, 31 g of oil 50620, and 4 g of an epoxidized polydimethylsiloxane oil bearing SiH groups of formula

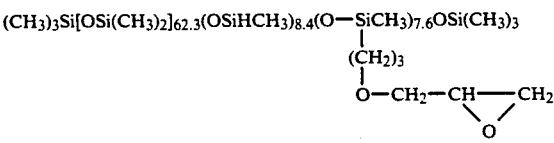

possessing a number average molecular mass Mn = 6,600.

The homogenization was carried out in the presence of 800 g of water and 18.2 g of CEMULSOL ON 10-20 emulsifier; the average particle diameter of the emulsion was 0.95 micron.

After crosslinking, a dispersion of particles whose average diameter was 0.70 micron, and containing 18.5% of magnetizable components, was obtained.

The degree of crosslinking was 91%.

EXAMPLE 16

The operation described in Example 1 was repeated, starting with:

13 g of the ferrofluid, which corresponds to 6.5 g of magnetizable pigment; and a solution of 800 g of cyclohexane, 31 g of Gum 789, marketed by RHONE-POULENC; this is a polydimethylsiloxane containing 700 ppm of SiVi groups along the molecular chain and having the following characteristics:

Viscosity = 13,000,000 mPas

Average degree of polymerization = 400,000; and 4 g of an epoxidized polydimethylsiloxane oil bearing SiH groups, of formula

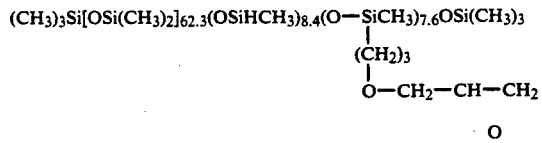

having a number average molecular mass Mn = 6,600.

The homogenization was carried out in the presence of 400 g of water and 9 g of CEMULSOL ON 10-20;

the average particle diameter of the emulsion was 1 micron.

After crosslinking for 4 hours of 40° C., a dispersion of particles whose average diameter was 0.8 micron, and containing 18.5% of magnetizable components, was obtained.

The degree of crosslinking was 98%.

TABLE I

| EXAMPLE | EMULSIFIER NATURE | EMULSIFIER QUANTITY g | EMULSION DIAM. MICRON | PARTICLES DIAM. MICRON | CROSSLINKING % | MAGNETIZATION e.m.u./g |
|---|---|---|---|---|---|---|
| 1 | ON 10-20 | 15.75 | 0.9  1 | 0.7  0.8 | 95 | / |
| 2 | Na LS | 15.75 | 0.9 | 0.85 | 97 | 6.8 |
| 3 | Na DBS | 15.75 | 1 | 0.85 | 98 | 6.9 |
| 4 | K 30 | 15.75 | 1.1 | 0.75 | 99 | 6.7 |
| 5 | KL | 15.75 | 1.3 | 0.65 | 97 | 6.1 |
| 6 | LTMA | 15.75 | 0.9 | 0.75 | 98 | 8 |
| 7 | ON 10-20 | 15.75 | 0.7 | 0.6 | 97 | 11.3 |
| 8 | ON 10-20 | 10.5 | 1 | 0.5 | 93 | 9 |

ON 10-20 = CEMULSOL ON 10-20 expressed as dry substance
Na LS = sodium lauryl sulfate
K 30 = $C_{13}$-$C_{17}$ Na alkylsulfonate, marketed by BAYER
KL = potassium laurate
LTMA = lauryl trimethylammonium chloride

TABLE II

| EXAMPLE | EMULSIFIER NATURE | EMULSIFIER QUANTITY g | EMULSION DIAM. MICRON | PARTICLES DIAM. MICRON | CROSSLINKING % | MAGNETIZATION e.m.u./g |
|---|---|---|---|---|---|---|
| 9 | ON 10-20 | 5.25 | 1.2 | 0.8 | 91 | 9 |
| 10 | ON 10-20 | 15.75 | 1 | 0.8 | 97 | 5.6 |
| 11 | ON 10-20 | 15.75 | 0.85 | 0.75 | 97 | 24 |
| 12 | ON 10-20 | 15.75 | 1.2 | 0.75 | 92 | 27 |
| 13 | ON 10-20 | 15.75 | 0.9 | 0.7 | 98 | 6.7 |
| 14 | LTMA | 15.75 | 1 | 0.8 | 32 | |
| 15 | ON 10-20 | 15.75 | 0.95 | 0.7 | 91 | |
| 16 | ON 10-20 | 7.78 | 1 | 0.8 | 98 | |

ON 10-20 = CEMULSOL ON 10-20 expressed as dry substance
LTMA = lauryl trimethylammonium chloride

What is claimed is:

1. A process for preparing magnetizable composite particles, comprising the steps of:
    introducing into an aqueous medium containing a surfactant a mixture of
    a solution of at least one organopolysiloxane SiVi containing, per molecule, at least two vinyl groups each linked to a silicon atom, said organopolysiloxane having a viscosity ranging from 20 to 30,000,000 mPas at 25° C., in an organic solvent having a boiling point below 100° C., or capable of forming with water an azeotrope having a boiling point below 100° C.,
    a solution of at least one organohydrogenopolysiloxane SiH containing, per molecule, at least three hydrogen atoms each linked to a silicon atom, said organohydrogenopolysiloxane having a viscosity ranging from 5 to 1,500 mPas at 25° C., in an organic solvent having a boiling point below 100° C., or capable of forming with water an azeotrope having a boiling point below 100° C.,
    and a magnetic fluid comprising magnetizable particles less than 300 angstroms in diameter, suspended in an organic carrier liquid which is a solvent for said polymers SiVi and SiH and has a boiling point below 100° C. or is capable of forming with water an azeotrope having a boiling point below 100° C.;
    homogenizing the medium obtained;
    performing a hydrosilylation of the polymers SiH and SiVi in an aqueous emulsions; and
    removing the organic solvents and the organic carrier liquid.

2. The process as claimed in claim 1, further comprising at least partially removing said water after said organic solvent and organic carrier are removed.

3. The process as claimed in claim 1, wherein the oroganopolysiloxane SiVi is represented by the formula R"R"RSiO(SiRR"'O)$_n$(SiR"'R'O)$_m$SiRR'R"

wherein:
the R radicals may be identical or different, and are selected from a $C_1$-$C_4$ alkyl radical, and a phenyl radical;
the R' radicals may be identical or different, and are selected from a $C_1$-$C_4$ alkyl radical, a phenyl radical, and a vinyl radical, the number of vinyl radicals being at least 2per macromolecule;
the R" radicals may be identical or different and are selected from a $C_1$-$C_4$ alkyl radical, a phenyl radical and an OH radical;
the R'" radicals may be identical or different and are selected from a $C_1$-$C_4$ alkyl radical, a phenyl and a radical -r-X, wherein r is a divalent organic radical and X is selected from an epoxy, hydroxy, carboxyl, aldehyde, ester, aceto-ester, mercapto, mercapto ester, mercaptoalkoxy, amino, alkylamino, dialkylamino, trialkylamino, quaternary ammonium, amino alcohol, amido, hydrazide, hydrazino, $C_1$-$C_3$ haloalkyl, cyano, cyanato,

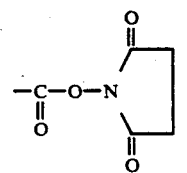

sulfate, sulfonyl and halobenzoyl group;

at least 60% of the R, R' and R" radicals are methyl radicals;

one of n or m can be zero, R' being a vinyl radical if m is zero, and n and m having a value sufficient to provide a polymer having a viscosity of 20 mPas to 30,000,000 mPas at 25° C., and, wherein the total number of -r-X units contributed by the organopolysiloxane SiVi and the organohydrogenopolysiloxane SiH ranges from 1:1 to 1,000:1 per molecule obtained from the hydrosilylation of organopolysiloxane SiVi with organohydrogenopolysiloxane SiH.

4. The process as claimed in claim 1, wherein the organohydrogenopolysiloxane SiH is of the formula $$YR_2SiO(RR'''SiO)_p(YRSiO)_qSiR_2Y$$

wherein the R radicals may be identical or different, and are selected from a $C_1$-$C_4$ alkyl radical and a phenyl radical, with at least 80% of R radicals being methyl radicals; the Y radicals may be identical or different and are selected from a $C_1$-$C_4$ alkyl radical, a phenyl radical and a hydrogen atom, the number of hydrogen atoms being at least 3 per molecule of polymer; and the radical R''' is selected from a $C_1$-$C_{14}$ alkyl radical, a phenyl radical and a radical -r-X, wherein r is a divalent organic radical and X is selected from an epoxy, hydroxy, carboxy, aldehyde, ester, aceto-ester, mercapto, mercapto ester, mercaptoalkoxy, amino, alkylamino, dialkylamino, trialkylamino, quaternary ammonium, amino alcohol, amido, hydrazide, hydrazino, $C_1$-$C_3$ haloalkyl, cyano, cyanato,

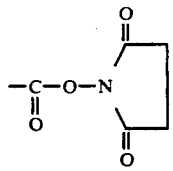

sulfate, sulfonyl and halobenzoyl group; p and q having a value sufficient to provide a polymer SiH having a viscosity ranging from 5 to 1,500 mPas at 25° C., and, wherein the total number of -r-X units contributed by the organopolysiloxane SiVi and the organohydrogenopolysiloxane SiH ranges from 1:1 to 1,000:1 per molecule obtained from the hydrosilylation of organopolysiloxane SiVi with organohydrogenopolysiloxane SiH.

5. The process as claimed in claim 1, wherein said aqueous medium contains from 0.5 to 15% of surfactant by weight and is employed in a quantity ranging from 0.5 to 60% of surfactant by weight relative to the weight of polymers SiVi and SiH.

6. The process as claimed in claim 3, wherein the divalent radical -r- is selected from $C_1$-$C_{18}$ linear alkylene radical, a $C_1$-$C_{18}$ branched alkylene radical, and a polyoxyalkylene radical containing from 1 to 50 $C_1$-$C_3$ oxyalkylene units.

7. The process as claimed in claim 6, wherein at least one of said $C_1$-$C_{18}$ alkylene radical and said $C_1$-$C_{18}$ branched alkylene radical is extended with groups selected from 1 to 5 divalent ethylenamine groups, 1 to 50 divalent $C_1$-$C_3$ alkylene oxide groups and a $$-O-CH_2-CH-CH_2-$$
$$\phantom{-O-CH_2-}|\phantom{CH-CH_2}$$
$$\phantom{-O-CH_2-}OH$$

group.

8. The process as claimed in claim 4, wherein the divalent radical -r- is selected from $C_1$-$C_{18}$ linear alkylene radical, a $C_1$-$C_{18}$ branched alkylene radical, and a polyoxyalkylene radical containing from 1 to 50 $C_1$-$C_3$ oxyalkylene units.

9. The process as claimed in claim 8, wherein at least one of said $C_1$-$C_{18}$ linear alkylene radical and said $C_1$-$C_{18}$ branched alkylene radical is extended with groups selected from 1 to 5 divalent ethylenamine groups, 1 to 50 divalent $C_1$-$C_3$ alkylene oxide groups and a $$-O-CH_2-CH-CH_2-$$
$$\phantom{-O-CH_2-}|\phantom{CH-CH_2}$$
$$\phantom{-O-CH_2-}OH$$

group.

10. The process as claimed in claim 1, wherein said magnetizable components present in the magnetic fluid are selected from magnetite, hematite, chromium dioxide, ferrites of manganese, nickel and manganese-zinc and alloys of cobalt, nickel, gadolinium and samarium-cobalt.

11. The process as claimed in claim 10, wherein the magnetizable particles present in the magnetic fluid are magnetite.

12. The process as claimed in claim 1, wherein the magnetic fluid contains from 20 to 60% by weight of magnetizable components.

13. The process as claimed in claim 12, wherein the weight magnetizable components in the magnetic fluid is 0.5 to 50% of weight of polymers SiVi and SiH.

14. The process as claimed in claim 13, wherein the solvent for the polymers SiH and SiVi and the carrier fluid of the magnetic fluid are the same or different and are selected from cyclohexane, methylene chloride, benzene, hexane, octane, toluene and carbon tetrachloride.

15. The process as claimed in claim 14, wherein the homogenization operation is carried out until droplets ranging in diameter from 0.065 to 3.2 microns are obtained.

16. The process as claimed in claim 15, wherein the hydrosilylation is carried out at a temperature ranging from 20° to 70° C., in the presence of a of a platinum group metal as hydrosilylation catalyst.

17. The process as claimed in claim 16, wherein the quantity of catalyst corresponds to 5 to 100 ppm, calculated as the weight of metal relative to the total weight of polymers SiVi and SiH.

18. The process as claimed in claim 17, wherein the solvents are removed before the hydrosilylation.

19. The process of claim 3, wherein at least one R radical is a 3,3,3-trifluoropropyl radical.

20. The process of claim 3, wherein at least one R' radical is a 3,3,3-trifluoropropyl radical.

21. The process of claim 3, wherein at least one R" radical is a 3,3,3-trifluoropropyl radical.

22. The process of claim 3, wherein at least one R''' radical is a 3,3,3-trifluoropropyl radical.

23. The process of claim 4, wherein at least one R radical is a 3,3,3-trifluoropropyl radical.

24. The process of claim 4, wherein at least one Y radical is a 3,3,3-trifluoropropyl radical.

25. The process of claim 4, wherein at least one R''' radical is a 3,3,3-trifluoropropyl radical.

* * * * *

UNITED STATES PATENT AND TRADEMARK OFFICE
CERTIFICATE OF CORRECTION

PATENT NO. : 5,108,636
DATED : April 28, 1992
INVENTOR(S) : Leising et al.

It is certified that error appears in the above-identified patent and that said Letters Patent is hereby corrected as shown below:

Claim 3, col. 14, line 5, "oroganopolysiloxane" should read --organopolysiloxane--;

line 7 (in the formula), the second occurrence of "R"" should read --R'--;

line 46, "2per" should read --2 per--.

Signed and Sealed this

Twelfth Day of October, 1993

Attest:

BRUCE LEHMAN

Attesting Officer

Commissioner of Patents and Trademarks